(12) United States Patent
Pernodet et al.

(10) Patent No.: US 9,877,916 B2
(45) Date of Patent: Jan. 30, 2018

(54) METHODS AND COMPOSITIONS FOR TREATING AGED SKIN

(71) Applicant: ELC Management LLC, Melville, NY (US)

(72) Inventors: Nadine Pernodet, Huntington Station, NY (US); Krystle Corallo, Huntington, NY (US); Dawn Layman, Ridge, NY (US); Donald Collins, Plainview, NY (US)

(73) Assignee: ELC Management LLC, Melville, NY (US)

(*) Notice: Subject to any disclaimer, the term of this patent is extended or adjusted under 35 U.S.C. 154(b) by 0 days.

(21) Appl. No.: 15/599,094

(22) Filed: May 18, 2017

(65) Prior Publication Data

US 2017/0252292 A1    Sep. 7, 2017

Related U.S. Application Data

(62) Division of application No. 15/002,878, filed on Jan. 21, 2016, now Pat. No. 9,687,439.

(51) Int. Cl.
| | |
|---|---|
| *A61K 8/97* | (2017.01) |
| *A61Q 1/10* | (2006.01) |
| *A61K 8/64* | (2006.01) |
| *A61K 35/20* | (2006.01) |
| *A61Q 19/08* | (2006.01) |
| *A61Q 19/10* | (2006.01) |
| *A61K 36/185* | (2006.01) |
| *A61Q 1/12* | (2006.01) |

(52) U.S. Cl.
CPC ............... *A61K 8/97* (2013.01); *A61K 8/64* (2013.01); *A61K 35/20* (2013.01); *A61K 36/185* (2013.01); *A61Q 1/10* (2013.01); *A61Q 1/12* (2013.01); *A61Q 19/08* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 2012/0195923 A1* | 8/2012 | Turgeon | A61K 8/975 424/195.17 |
| 2015/0209395 A1* | 7/2015 | Raskin | A61K 36/185 424/776 |

FOREIGN PATENT DOCUMENTS

JP    2012-232915 A    * 11/2012

OTHER PUBLICATIONS

Wang (Journal of Cosmetic and Laser Therapy (2013), vol. 15, No. 237-241).*

* cited by examiner

*Primary Examiner* — Susan Hoffman
(74) *Attorney, Agent, or Firm* — Julie Blackburn

(57) ABSTRACT

A composition comprising an extract from damaged plant parts from the Moringaceae genus, at least one oligopeptide, at least one extract from the *Laminaria* genus, and whey protein and a method for stimulating collagen synthesis in skin cells.

18 Claims, No Drawings

METHODS AND COMPOSITIONS FOR TREATING AGED SKIN

This application is a divisional application of U.S. application Ser. No. 15/002,878, filed Jan. 21, 2016, now U.S. Pat. No. 9,687,439.

TECHNICAL FIELD

The invention is in the field of compositions for treating aging skin, and with particular efficacy in stimulating synthesis of collagen in skin cells.

BACKGROUND OF THE INVENTION

Collagen is one of the main structural proteins in skin. It can be found in the fibrillar or non-fibrillar form. The fibrillar form is most common and includes collagen subtypes I, II, III, V, and XI. Types I, IV, and V are most often associated with skin and dermal tissue. Collagen found in the skin typically diminishes with age and causes laxity, lines, and wrinkles on skin. Any active ingredient that induces skin cells to increase collagen synthesis is desirable because it ameliorates the adverse effects of collagen deficiency in skin cells which causes lines, wrinkles, and skin laxity.

It has been discovered that an extract obtained from damaged plant parts from Moringaceae genus in combination with a complex of actives exhibits dramatically improved stimulation of collagen synthesis in skin cells that is dose/response sensitive. This is most unexpected because the Moringaceae extract alone exhibits no, or even decreased, activity in stimulating collagen synthesis in skin cells.

SUMMARY OF THE INVENTION

The invention is directed to a topical composition comprising at least one extract from damaged plant parts from a plant from the Moringaceae genus, at least one oligopeptide, at least one extract from the *Laminaria* genus, and whey protein.

The invention is also directed to a method for stimulating collagen synthesis in skin cells by topically applying the composition.

DETAILED DESCRIPTION

The invention comprises a combination of an extract obtained from injured plant parts from the Moringaceae genus, at least one oligopeptide, at least one extract from the *Laminaria* genus, and whey protein. The composition of the invention may be in the liquid, semi-solid, or solid form, and may be in the emulsion, solution, suspension, or anhydrous form. If in the solution or suspension form, the composition may contain from about 50 to 99.9% water. If in the emulsion form, the composition may contain from about 5-95% water and from about 5-95% oil. If in the anhydrous form, the composition may comprise from about 10-99% oil and 10-99% solidifying agents.

The Extract from the Moringaceae Genus

The composition contains at least one extract obtained by extraction of damaged plant parts from a plant of the Moringaceae genus. The extract may present in amounts ranging from 0.01 to 5%, preferably from about 0.05 to 3%, more preferably from about 0.1 to 2% by weight of the total composition.

Plants from this genus grow prevalently in Africa and India. Moringaceae is a genus of flowering plants that vary in size from large trees to small flowering plants. There are 13 species. The species *drouhardii, hildebrandtii, ovalifolia*, and *stenopetala* are massive trees with large water storing trunks ("bottle trees") and small radial and symmetrical flowers. The species *concanensis, oleifera*, and *peregrina* are slender trees with a tuberous juvenile stage and pale white or pink flowers. The species *arborea, borziana, longituba, pygmaea, rivae, ruspoliana* in the form of trees, shrubs, or herbs. *Moringa oleifera* in particular is a fast growing tree that is often referred to as the "drumstick tree". *Moringa* leaves are said to contain high amounts of vitamins, polyphenols and four unique sugar modified aromatic glycosides. Isothiocyanates from Moringaceae are said to have many health benefits. *Moringa* isocthiocyanates ("MIC"). In general, isothiocyanates are formed when an enzyme, myrosinase (aka thioglucoside glycohydrolase), cleaves thio-linked glucose in precursor glucosinolates. Moringaceae extracts with higher concentrations of MICs are most desirable. Such extracts can be prepared by injuring the plant parts to cause an increase in the myrosinase enzyme content, which in turn will promote conversion of *Moringa* glucosinolates ("MGL") into MICs.

Moringaceae extracts that may be used in the compositions of the invention are further described in Phytochemistry, Vol 103 (2014), pages 114-122; and U.S. provisional patent application Ser. Nos. 61/898,795 filed Nov. 1, 2013; 62/032,496, filed Aug. 1, 2014; and U.S. Ser. No. 14/683, 730, a continuation-in-part of PCT/US2014/0063178, filed Oct. 30, 2014, all being incorporated by reference in their entirety.

Injuring the plant parts can occur by processing steps such as pressing, slicing, pulverizing, crushing, blending, or grinding. Injury (and myrosinase production) can also be induced by subjecting the plant parts to a solution containing water. This solution may be all water, or a mixture of water of various solvents such as ethanol, propanol, isopropanol, butylene glycol propylene glycol, pentylene glycol, and so on. It is preferred that such injury occur at temperatures lower than 100° C. and without otherwise exposing the plant parts to extreme weather conditions such as low temperatures or harsh drying conditions. The conditions inducing plant injury should take place for a period of time sufficient to activate the myrosinase enzyme in an amount sufficient to cause increased production of MICs in the injured plant parts.

The plant parts that may be used include stems, leaves, roots, sprouts, seeds, twigs, flowers, bark, etc. Most preferred is where the plant parts that are injured are from seeds, sprouts, or leaves. It is preferred that the plant parts are fresh, that is, they have not been dried or frozen.

After injury of the plant parts, they may be extracted or dried. Suitable extractants may be water or mixtures of water and solvents as noted above. The injured plant parts may be extracted immediately, or extracted after drying.

Suitable extractants include water, alkanes, ethers, aromatic solvents, ketones and the like. Preferred is water alone, water/solvent mixtures, or solvent alone where the solvents comprise mono-, di-, or polyhydric alcohols such as ethanol, propanol, isopropanol, butanol, methanol. The extractant may be combined with the plant parts in any suitable ratio including 1:1-10 to 1-10:1 ratio of solvent/water respectively.

It is preferred that the concentration of MIC in the extract should be at least 0.5 to 10% of MICs per gram of plant material, preferably 0.75 to 4%, more preferably from 0.8 to 5%. Harsh temperatures or drying of plant parts will cause rapid degradation of the MICs present in the plant parts and resulting extract.

Most preferred is *Moringa oleifera* seed extract containing from about 0.5 to 3.0% MICs, more preferably 0.75 to 2.5% MIC, most preferably from about 0.8 to 1.5% MICs. This extract may be purchased from Nutrasorb LLC under the trade name Nutringa® which is mixture of *Moringa oleifera* seed extract and isoceteth-20 in a ratio of about 7.5 to 92.5 respectively, and containing about 1% MIC. The MIC content of the best embodiment extract when tested for stability at 25° C. and 37° C. for 30 days is greater than 65%, preferably greater than 70%.

The Oligopeptide

The composition contains at least one oligopeptide in an amount ranging from about 0.000001 to 5%, preferably from about 0.00001 to 2%, more preferably from about 0.0005 to 1% by weight of the total composition.

Suitable oligopeptides are those having from about 2 to 20, preferably from about 4 to 10, or most preferably 5 to 6 amino acids. The peptides may be substituted with acyl groups such as acetyl, palmitoyl, and the like. Examples of suitable oligopeptides include but are not limited to dipeptides, tripeptides, pentapeptides, hexapeptides, heptapeptides, and so on. Suitable acyl groups include acetyl, palmitoyl, or myristoyl. Further specific examples include hexapeptides 1-60, said range including each whole integer between 1 and 60, hexapeptides that are acetylated, palmitoylated or myristoylated such as acetyl hexapeptides 1, 7, 8, 19, 20, 22, 24, 30, 31, 37, 38, 39, or 40. Particularly preferred is Acetyl Hexapeptide-8 which is obtained by the acetylation of Hexapeptide-8, a synthetic peptide containing arginine, glutamic acid, glutamine, and methionine. Acetyl Hexpeptide-8 can be purchased from Lipotec S.A. under the tradename Argireline®, which is a solution of about 0.05 parts Acetyl Hexpeptide-8, 93.35 parts water, with the remainder preservatives.

Also suitable are pentapeptides which may be acetylated, palmitoylated, or myristoylated. Examples of such pentapeptides include Pentapeptides 1-50 which includes each integer inbetween. Particularly preferred is Palmitoyl pentapeptide-5.

Particularly preferred are oligopeptides having the INCI names Acetyl-hexapeptide-8, Palmitoyl oligopeptide, Tripeptide-32, Tetrapeptide-26, Palmitoyl hexapeptide-12, Oligopeptide-10, Oligopeptide-5, Oligopeptide-3, Pentapeptide-3, Tetrapeptide-51 amide, Heptapeptide, Palmitoyl pentapeptide-5 or combinations thereof. These peptides are defined by the International Nomenclature for Cosmetic Ingredients (INCI) and are terms known in the art.

The Extract from *Laminaria* Genus

The composition contains at least one extract from the *Laminaria* genus. *Laminaria* is a genus that contains 30+ species of the brown algae Phaeophyceae, often referred to as kelp. Such extracts from the *Laminaria* genus include those of species *abyssalis, agardhii, appressirhiza, brasiliensis, brongardiana, bulbosa, bullata, complanata, digitata, ephemera, farlowii, groenlandica, hyperborea, inclinitorhiza, multiplicata, nigripes, ochroleuca, pallida, platymeris, rodriguezi, ruprechtii, sachalinensis, setchellii, sinclairii, solidungula,* or *yezoensis*. Preferred is where the extract from the *Laminaria* genus is also a SIRT3 activator. Preferred is where the extract is from *Laminaria digitata*, and more specifically an extract having laminarin content and/or a mannitol content ranging from 0.5 to 3% by weight, or from about 0.75 to 2.5%, by weight, or most preferably from about 1% by weight or greater, preferably around 2%.

An example of a suitable extract of *Laminaria digitata* may be purchased from Barnet Products under the tradename Mitostime Di which is a mixture of 91 parts water, 8 parts *Laminaria digitata* extract, and 1 part preservative. Preferably the *Laminaria digitata* extract is obtained by aqueous extraction and leaching of lyophilized algae and sterilizing the microfiltration, followed by reverse osmosis to concentrate the active molecules.

In the preferred embodiment of the invention the extract may be present in the composition in amounts ranging from 0.0001 to 5%, preferably from about 0.001 to 2.5%, more preferably from about 0.01 to 1%.

Whey Protein

The composition contains whey protein, in an amount ranging from 0.01 to 5%, preferably from about 0.05 to 3%, more preferably from about 0.1 to 2% by weight of the total composition.

Whey protein is the polypeptide obtained from the fluid part of milk after separation from curds. The whey protein may be hydrolyzed. Most preferred is a whey protein sold by Glanbia Foods having the trade name whey protein NXP.

In one embodiment, the oligopeptide, *Laminaria* extract and whey protein may be supplied to the composition in the form of a pre-blend that can then be formulated into the final product. In this case a ratio of from about 2-20 parts of oligopeptide, 1-10 parts *Laminaria* extract, and 0.1 to 5 parts whey protein is appropriate. Most preferred is a ratio of 10 parts Acetyl hexapeptide-8, 5 parts *Laminaria digitata* extract, and 1 part whey protein. The composition of the invention may consist of the extract from damaged plant parts of Moringaceae genus, the oligopeptide, the extract from the *Laminaria* genus, and whey protein and no other ingredients.

The composition of the invention may also "consist essentially of" the extract from damaged plant parts of Moringaceae genus, the oligopeptide, the extract from the *Laminaria* genus, and whey protein, which means a composition that contains the four ingredients mentioned and only additional ingredients that do not affect that basic and novel characteristics of the composition such as water, preservatives, antioxidants, pH adjusters, solvents, and inert ingredients that do not affect the collagen stimulating activity of the composition.

The composition of the invention may also "comprise" the four ingredients mentioned and include other ingredients including but not limited to those set forth herein.

Other Ingredients

Oils

Suitable oils include silicones, esters, vegetable oils, synthetic oils, including but not limited to those set forth herein. The oils may be volatile or nonvolatile, and are preferably in the form of a pourable liquid at room temperature. If present, the oils may range from about 0.5 to 85%, preferably from about 1-75%, more preferably from about 5-65% by weight of the total composition.

Cyclic and linear volatile silicones are available from various commercial sources including Dow Corning Corporation and General Electric. The Dow Corning linear volatile silicones are sold under the trade names Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

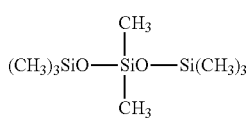

purchased from Shin-Etsu Silicones under the trade name TMF-1.5, having a viscosity of 1.5 centistokes at 25° C.

Also suitable are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

Also suitable are esters formed by the reaction of a carboxylic acid and an alcohol. The alcohol and the carboxylic acids may both have fatty (C6-30) chains. Examples include hexyl laurate, butyl isostearate, hexadecyl isostearate, cetyl palmitate, isostearyl neopentanoate, stearyl heptanoate, isostearyl isononanoate, stearyl lactate, stearyl octanoate, stearyl stearate, isononyl isononanoate, and so on.

The ester may also be in the dimer or trimer form. Examples of such esters include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

Examples of other types of esters include those from arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone. Examples include dimethicone, phenyl dimethicone, diphenyl dimethicone, phenyl trimethicone, or trimethylsiloxyphenyl dimethicone. Other examples include alkyl dimethicones such as cetyl dimethicone, stearyl dimethcone, behenyl dimethicone, and the like.

Surfactants

The composition may contain one or more surfactants, especially if in the emulsion form. However, such surfactants may be used if the compositions are anhydrous also, and will assist in dispersing ingredients that have polarity, for example pigments. Such surfactants may be silicone or organic based. The surfactants will aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

Silicone surfactants may be generically referred to as dimethicone copolyol or alkyl dimethicone copolyol. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of crosslinked silicone surfactants that are often referred to as emulsifying elastomers that contain at least one hydrophilic moiety such as polyoxyalkylenated groups. Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on. All recitations of units include all whole integers between the range.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

Humectants

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol.

Botanical Extracts

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina Pavonica* extract, *thermus thermophilus* ferment extract, *camelina sativa* seed oil, *boswellia serrata* extract, olive extract, *Aribodopsis Thaliana* extract, *Acacia Dealbata* extract, *Acer Saccharinum* (sugar maple), acidopholus, acorns, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza Glabra, Salix Nigra, Macrocycstis Pyrifera, Pyrus Malus, Saxifraga Sarmentosa, Vitis Vinifera, Morus Nigra, Scutellaria Baicalensis, Anthemis Nobilis, Salvia Sclarea, Rosmarinus Officianalis, Citrus Medica Limonum, Panax Ginseng, Siegesbeckia Orientalis, Fructus Mume, Ascophyllum Nodosum*, Bifida Ferment lysate, *Glycine Soja* extract, *Beta Vulgaris, Haberlea Rhodopensis, Polygonum Cuspidatum, Citrus Aurantium Dulcis, Vitis Vinifera, Selaginella Tamariscina, Humulus Lupulus, Citrus Reticulata* Peel, *Punica Granatum, Asparagopsis, Curcuma Longa, Menyanthes Trifoliata, Helianthus Annuus, Hordeum Vulgare, Cucumis Sativus, Evernia Prunastri, Evernia Furfuracea*, and mixtures thereof.

Particulate Materials

The compositions of the invention may contain particulate materials in the form of pigments, inert particulates, or mixtures thereof. If present, suggested ranges are from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

The particulate matter may be colored or non-colored powders. Suitable non-pigmented powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

Suitable pigments are organic or inorganic. Organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

Vitamins and Antioxidants

The compositions of the invention may contain vitamins and/or coenzymes, as well as antioxidants. If so, 0.001-10%, preferably 0.01-8%, more preferably 0.05-5% by weight of the total composition is suggested. Suitable vitamins include ascorbic acid and derivatives thereof such as ascorbyl palmitate, tetrahexydecyl ascorbate, and so on; the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are retinyl palmitate, retinol. retinoic acid, as well as Vitamin A in the form of beta carotene. Also suitable is Vitamin E and derivatives thereof such as Vitamin E acetate, nicotinate, or other esters thereof. In addition, Vitamins D and K are suitable.

The invention further comprises treating skin to stimulate collagen synthesis by topically applying a composition comprising an extract from damaged plant parts of Moringaceae genus, at least one oligopeptide, at least one extract from the *Laminaria* genus, and whey protein. The compositions may be applied in the forms mentioned herein, as part of skin care regimens. For example, the composition may be applied to the skin as a night cream or cream applied to skin prior to a period of bodily rest such as a nap or sleep. The composition may be applied two times a day, in the morning and in the evening after cleansing the skin. The composition may be applied to the skin over skin care products, in the form of foundations or other color cosmetics.

The invention will be further described in connection with the following examples which are set forth for the purposes of illustration only.

Example 1

*Moringa oleifera* seed extract was tested at various concentrations for its ability to stimulate collagen production in normal human dermal fibroblasts ("NHDF") from a 40 year old donor in a collagen induction assay. *Moringa oleifera* extract diluted in dimethylsulfoxide ("DMSO") (% concentrations 0.003125, 0.00625 and 0.0125), *Moringa oleifera* exract diluted in Dulbecco's Modified Eagle Medium supplemented with 10% Hyclone® bovine calf serum and 1% Cellgro® penicillin-streptomycin solution ("DMEM") (% concentrations of 0.0000625, 0.000125, 0.00025, 0.0005), positive control (L-ascorbic acid, 18 ug/ml), and DMEM alone were tested.

Cell Growth and Maintenance. Aged NHDF were obtained from ZenBio. Fibroblasts were cultured in DMEM 1× (Life Tech) supplemented with 10% bovine calf serum (Hyclone) and 1% PenStrep solution (Cellgro). Cells were regularly maintained; subcultured as needed.

Plating Cells.

Normal human dermal fibroblasts (NHDF, aged) were plated on a 96-well plate in supplemented DMEM (as indicated above). All rows, except for Row A, were seeded with cells (Row A was left blank to allow for background subtraction). Plate was allowed to incubate at standard conditions (37° C., 5% $CO_2$, 95% humidity) overnight.

Preparation & Treatment of Cells.

The following treatments were created in full media (1% P/S and 10% BCS supplemented) DMEM: (1) *Laminaria digitata* extract (0.5%), Acetyl hexapeptide-8 (1%) and whey protein (0.1%, solid) mixture alone; (2) Mixture+*Moringa oleifera* extract (0.000125%); (3) Mixture+*Moringa oleifera* extract (0.00025%); (4) Mixture+*Moringa oleifera* extract (0.00035%); and (5) Mixture+*Moringa oleifera* extract (0.0005%). Each treatment (200 ul/well) was added to the corresponding well of the 96-well plate. Treated plate was allowed to incubate at standard conditions (37° C., 5% $CO_2$, 95% humidity) for 72 hr.

Viability Assay.

Following 72 hours of incubation, supernatants were harvested and stored prior to collagen analysis. A 10% alamar blue (Life Tech) solution was created in warmed (37° C.) full media and assay was completed exactly as per manufacturer's (Life Tech) protocol. Alamar Blue results were determined using a plate reader. Data was analyzed using the SoftMax Pro software and Excel.

Assessment of Collagen Production.

Collagen production was assessed using the Pro-collagen Type I collagen EIA Kit (Takara) as per manufacturer's protocol, exactly as described. Plate was read using the Gemini M2E plate reader and results were compared.

The results are set forth below and show that the *Moringa oleifera* seed extract exhibits varying levels of efficacy in stimulating collagen synthesis in NHDF at varying concentrations. In particular, the collagen stimulating activity is not dose dependent and also appears to vary based upon whether diluent is DMEM or DMSO. The results are set forth below:

| Test Material | Concentration | % increase in collagen induction |
| --- | --- | --- |
| L-ascorbic acid (+Control) | 18 ug/ml | +16 |
| *Moringa* extract (DMEM) | 0.0000625 | −13 |
| *Moringa* extract (DMEM) | 0.000125 | +8 |
| *Moringa* extract (DMEM) | 0.00025 | −22 |
| *Moringa* extract (DMEM) | 0.0005 | −20 |
| *Moringa* extract (DMSO) | 0.003125 | −22 |
| *Moringa* extract (DMSO) | 0.00625 | −3 |
| *Moringa* extract (DMSO) | 0.0125 | −11 |

In general it is seen that *Moringa oleifera* extract itself does not have activity in stimulating collagen production in NHDF, and in fact, in most cases, causes decreased collagen synthesis.

Example 2

The combination of *Moringa oleifera* seed extract and a mixture of Acetyl hexapeptide-8, *Laminaria digitata* extract and whey protein were tested for collagen stimulation in NHDF from a 40 year old donor. Increasing concentrations of *Moringa oleifera* extract were combined with a mixture of a 1% solution of Acetyl hexapeptide-8 solution, 0.5% *Laminaria digitata* extract solution, and 0.1% whey protein in Supplemented DMEM.

The tests were performed according to the method in Example 1. The results are set forth below:

| Test Material: | Percent Increase in Collagen Synthesis over Mixture Alone (%) |
|---|---|
| Mixture + 0.0001% *Moringa oleifera* extract | 4.50 |
| Mixture + 0.0002% *Moringa oleifera* extract | 6.60 |
| Mixture + 0.0003 *Moringa oleifera* extract | 12.00 |
| Mixture + 0.0004 *Moringa oleifera* extract | 16.54 |
| Mixture + 0.0005 *Moringa oleifera* extract | 22.00 |
| Mixture + 0.0006 *Moringa oleifera* extract | 35.19 |

The above results show that addition of increasing concentrations of *Moringa oleifera* extract to the Mixture provided a dose response increase in collagen synthesis in fibroblasts. As noted in Example 1, *Moringa oleifera* extract itself largely causes decreased collagen synthesis in fibroblasts, and exhibits no dose response relationship to increasing concentrations.

Example 3

A skin care composition according to the invention was made as follows:

| Ingredient | % by weight |
|---|---|
| Water | QS100 |
| Isononyl isononanoate | 6.0 |
| C12-20 acid PEG-8 ester | 3.0 |
| Glycerin | 2.6 |
| Dimethicone | 1.5 |
| Shea butter | 1.5 |
| Cetyl alcohol | 1.4 |
| Butylene glycol | 1.2 |
| PEG-100 stearate | 0.75 |
| Acetyl glucosamine | 0.50 |
| Sucrose | 0.50 |
| Preservatives | 1.0 |
| Ammonium acryloyldimethyl taurate | 0.35 |
| Sorbitol | 0.35 |
| Pentylene glycol | 0.25 |
| Algae extract | 0.25 |
| Caffeine | 0.20 |
| Carbomer | 0.20 |
| Potassium cetyl phosphate | 0.20 |
| Tocopheryl acetate | 0.20 |
| Ethylhexylglycerin | 0.15 |
| Aquacell* | 1.00 |
| Acrylates/C10-30 alkyl acrylates crosspolymer | 0.11 |
| Phytofix** | 0.20 |
| Whey protein | 0.10 |
| Glucose | 0.10 |
| Isoceteth-20 | 0.10 |
| *Laminaria digitata* extract | 0.04 |
| *Moringa oleifera* seed extract (1% MIC) | 0.01 |
| Acetyl hexapeptide 8 | 0.01 |

*Aquacell: a mixture of water, *Citrullus lanatus* (watermelon) fruit extract, *Pyrus malus* (apple) fruit extract, *Lens esculenta* (Lentil) fruit extract, sodium lactate, and sodium PCA.
**Phytofix: a mixture of propylene glycol dicaprate, *Helianthus annus* (sunflower) seed cake, *Hordeum vulgare* (barley) extract, *Cucumis sativus* (cucumber) fruit extract.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

The invention claimed is:

1. A method for stimulating collagen synthesis in skin cells by applying a composition comprising an extract from live, damaged plant parts from the *Moringa* genus which release myosinase enzyme in an amount sufficient to cause the extract to contain *Moringa* isothiocyanates, in combination with a mixture of an oligopeptide, an extract from the *Laminaria* genus, and whey protein.

2. The method of claim 1 wherein the composition is applied in the form of a skin cream or lotion.

3. The method of claim 1 wherein the composition is applied once or twice per day.

4. The method of claim 1 wherein the extract from *Moringa* genus has a *Moringa* isothiocyanate concentration ranging from 0.5 to 3.5% by weight of the total *Moringa* extract.

5. The method of claim 1 wherein the oligopeptide is selected from an acetylated peptide, a palmitoylated peptide, a myristolated peptide, or combinations thereof.

6. The method of claim 5 wherein the extract from the *Moringa* genus is *Moringa oleifera*, the oligopeptide is an acetylated peptide which is Acetyl hexapeptide-8, and the extract from *Laminaria* genus is *Laminaria digitata*.

7. The method of claim 6 wherein the composition is in the form of an emulsion.

8. The method of claim 1 wherein the oligopeptide is an acetylated, or palmitoylated peptide.

9. The method of claim 8 wherein the oligopeptide is a hexapeptide.

10. The method of claim 9 wherein the hexapeptide is an acetylated hexapeptide.

11. The method of claim 10 wherein the acetylated hexapeptide is acetyl hexapeptide-8.

12. The method of claim 1 wherein the *Laminaria* genus is *Laminaria digitata*.

13. The method of claim 1 wherein the stimulation of collagen synthesis in skin cells is demonstrated on fibroblasts tested in vitro.

14. The method of claim 13 wherein the stimulation in collagen synthesis in skin cells is a dose/response increase in collagen synthesis.

15. A method for stimulating collagen synthesis in skin cells by applying an aqueous based composition comprising an extract from live, damaged plant parts from the *Moringa* genus which release myosinase enzyme in an amount sufficient to cause the extract to contain from about 0.5 to 3.5% by weight of the total extract of *Moringa* isothiocyanates; at least one oligopeptide; an extract from the *Laminaria* genus, and whey protein.

16. The method of claim 15 wherein the oligopeptide is an acetylated peptide, a myristoylated peptide, a palmitoylated peptide, or combinations thereof.

17. The method of claim 16 wherein the extract from the *Laminaria* genus is *Laminaria digitata*.

18. The method of claim 15 wherein the aqueous based composition is an emulsion.

* * * * *